United States Patent
Wölfel et al.

(10) Patent No.: US 8,430,869 B2
(45) Date of Patent: Apr. 30, 2013

(54) LASER DEVICE FOR OPHTHALMOLOGICAL LASER SURGERY

(75) Inventors: Mathias Wölfel, Erlangen (DE); Olaf Kittelmann, Berlin (DE); Daniel Thürmer, Nürnberg (DE)

(73) Assignee: Wavelight GmbH, Erlangen (DE)

( * ) Notice: Subject to any disclaimer, the term of this patent is extended or adjusted under 35 U.S.C. 154(b) by 173 days.

(21) Appl. No.: 12/965,349

(22) Filed: Dec. 10, 2010

(65) Prior Publication Data

US 2012/0150157 A1 Jun. 14, 2012

(51) Int. Cl.
 *A61B 18/20* (2006.01)
(52) U.S. Cl.
 USPC ...................................... 606/4; 606/5; 606/10
(58) Field of Classification Search .................. 606/4–6, 606/10–12; 351/205–212
 See application file for complete search history.

(56) References Cited

U.S. PATENT DOCUMENTS

| | | | |
|---|---|---|---|
| 6,706,036 B2 * | 3/2004 | Lai | 606/12 |
| 2002/0097378 A1 | 7/2002 | Saito et al. | |
| 2002/0193704 A1 | 12/2002 | Goldstein et al. | |
| 2004/0199149 A1 * | 10/2004 | Myers et al. | 606/4 |
| 2005/0030477 A1 * | 2/2005 | Lai et al. | 351/233 |
| 2007/0173794 A1 | 7/2007 | Frey et al. | |
| 2009/0118718 A1 | 5/2009 | Raksi et al. | |
| 2010/0114079 A1 * | 5/2010 | Myers et al. | 606/5 |

OTHER PUBLICATIONS

Unknown; "PID Controller"; printed Aug. 8, 2011, Wikipedia, http://en.wikipedia.org/wiki/PID_controller; 17 pages.

* cited by examiner

*Primary Examiner* — Ahmed Farah
(74) *Attorney, Agent, or Firm* — Keiko Ichiye

(57) ABSTRACT

A laser device, in particular for ophthalmological laser surgery, comprising a laser source (14) for providing laser radiation, controllable scan components (20) for setting a focus position of the laser radiation, measuring components (30) for registering information that is representative of an actual position of the radiation focus, and also a control arrangement (22) controlling the laser source and the scan components. In accordance with the invention, the control arrangement can be set up to bring about the implementation of a test-mode operation of at least some of the scan components with the laser source turned off, in accordance with a predetermined test scan pattern, the test scan pattern representing a plurality of discrete desired focus positions to be traversed in succession, and the control arrangement having been set up to stop, at each of the desired focus positions, the scan movement of the scan components and to ascertain, assigned to each of the desired focus positions, respectively an actual focus position on the basis of the registered information of the measuring components.

9 Claims, 1 Drawing Sheet

LASER DEVICE FOR OPHTHALMOLOGICAL LASER SURGERY

TECHNICAL FIELD

The present invention relates to laser devices and, more particularly, to the testing of a scan function of a laser device.

BACKGROUND

Laser devices that operate with focused laser radiation in order to machine inorganic or organic material (e.g., human eye tissue) frequently exhibit controllable components that enable a scan function. With the scan function the radiation focus can be set precisely to differing positions in a plane orthogonal to the direction of propagation of the radiation (transverse scanning) or/and to differing positions along the direction of propagation of the radiation (longitudinal scanning). Examples of components that can serve for the scanning of laser radiation are swivel-mounted mirrors, deformable mirrors, electro-optical crystals, displaceably arranged lenses, lenses of variable refractive power, etc. Whenever scan components are mentioned within the scope of this disclosure, not only the optical components acting on the laser radiation are meant thereby, but rather also the totality of the components that are needed for scanning the laser radiation and that are capable of being influenced by electrical control signals of an electronic control arrangement. Accordingly, the scan components in the sense of the invention also include, in particular, the actuators that, where appropriate, are necessary for actuating the optical scan components and that are capable of being driven by the control signals of the control arrangement. Such actuators may, for example, include galvanometer drives, piezoelectric drives, motorized drives, controllable voltage-sources or current-sources, etc. It will be understood that the above enumeration of possible optical scan components and actuators is purely exemplary and is not to be understood as being restrictive.

SUMMARY

The embodiments of the present invention provide a laser device that may be intended and set up for ophthalmological laser surgery, comprising a laser source for providing laser radiation, controllable scan components for setting a focus position of the laser radiation, measuring components for registering information that is representative of an actual position of the radiation focus, and also a control arrangement controlling the laser source and the scan components, which has been set up to bring about the implementation of a test-mode operation of at least some of the scan components with the laser source turned off, in accordance with a predetermined test scan pattern, the test scan pattern representing a plurality of discrete desired focus positions to be traversed in succession, and the control arrangement set up to stop the scan movement of the scan components at each of the desired focus positions and to ascertain, assigned to each of the desired focus positions, respectively, an actual focus position on the basis of the registered information of the measuring components. The test-mode operation is, as it were, a dry run in which the scan function of the laser device can be examined without laser radiation being given off by the laser device at the same time.

Ageing phenomena, a relative long period of disuse and/or interruptions in the data-transfer paths may have the result that a desired setting of the scan components ordered by the control arrangement (corresponding to a particular desired position of the radiation focus) is not realized precisely and the actual setting of the scan components that is in fact achieved differs from the desired setting. With the laser source turned on, the actual position of the radiation focus would then differ from the desired position. In the case of the machining of dead or inorganic matter this may be acceptable, insofar as the machining can be repeated with a new workpiece if it turns out that the first machining was not sufficiently precise. In the case of living tissue—such as human eye tissue, for example—such a manner of proceeding is not feasible, for comprehensible reasons. The implementation of a prior test-mode operation of the scan components can provide certainty that in the course of the subsequent laser machining the desired value and the actual value are in fact sufficiently exactly close together, or/and it can provide elucidation about the extent of any possible deviations between desired and actual values, so that prior to the laser machining suitable corrective measures (e.g. exchange of at least some of the scan components, ascertainment of correction factors and adaptation of the desired values on the basis of the correction factors) can still be instigated.

The test scan pattern represents a plurality of discrete desired focus positions to be traversed individually, the scan components (generally, the scan system) being controlled by the control arrangement in such a manner that the scan movement brought about by the scan components stops in each instance at the desired focus positions, so that the actual focus positions are measured at a standstill. With the measurement of the actual focus position in each instance a wait is observed for a certain time (settling-time) after the scan components have reached a desired focus position. This settling-time may, for example, be of the order of magnitude of one or more milliseconds. By the measurement of the actual focus positions being effected at a standstill, it is possible to utilize the maximally possible measuring accuracy of the measuring components (measuring device).

The desired focus positions can be distributed in such a way that all the regions of the nominally available scan space are covered. In this way, an extensive advance inspection of the positioning accuracy of the scan function in all traversable regions of the scan space is possible. Through the choice of not too large a number of desired focus positions, at the same time the inspection procedure can be kept short, enabling, in particular, the test-mode operation to be carried out prior to each planned laser machining without losing much time unnecessarily. For example, it may be sufficient to define in advance less than 100, better less than 50, and still better less than 20, desired focus positions which are to be traversed within the scope of the test-mode operation.

It will be understood that the reference to desired and actual focus positions serves only for mental clarification, since in the test-mode operation no laser radiation impinges on the scan components and, accordingly, also no radiation focus is present. With the laser source switched on, the radiation focus that is then present would, of course, occupy a position that is given by the actual setting of the scan components.

Typically, the region within which the radiation focus can be adjusted is limited by constructional, physical or/and control-engineering presets. In this way, the user has a predetermined maximal scan field available which defines the outer boundaries for the scan movements of the radiation focus. In embodiments of the present invention that enable solely transverse focus movements, the available scan field is accordingly a transverse surface. On the other hand, in embodiments that enable transverse and longitudinal focus movements, the available scan field is a three-dimensional space. Transversely the available scan field may have, for example, a circular outer boundary. In the three-dimensional case the available scan field may, for example, have a circular cylindrical shape.

At least in some cases it may be that the available scan field is to be utilized for an application right up to its boundaries. Not only then, but particularly then, it is important to have certainty that also in the marginal regions of the available scan field the scan components are operating precisely and desired/actual deviations of the focus position only arise, if at all, within tolerable limits. Therefore, in certain embodiments of the present invention at least a fractional number of the desired focus positions can be arranged at the margin of a given maximal scan field. The embodiments of the present invention can further provide for arranging all the desired focus positions at the margin of the maximally possible scan field.

The desired focus positions may include at least one group of focus positions that are arranged in distributed manner in a transverse plane orthogonal to the direction of propagation of the radiation. In this case the desired focus positions may include at least one group of focus positions that are arranged in distributed manner in the transverse plane along a circular line, in particular at regular angular distances. For example, it may be sufficient to define only a few desired focus positions along the circular line, for instance one desired focus position per quadrant.

In the case of longitudinal scan capability of the scan components, at least some of the desired focus positions may be arranged in a distributed manner in the direction of propagation of the radiation. In particular, it is contemplated that the desired focus positions include several groups of focus positions that are arranged in a distributed manner in various transverse planes orthogonal to the direction of propagation of the radiation. In this case, for example, a first group of desired focus positions may lie in a first transverse plane that delimits the available scan field longitudinally in a first direction. A second group of desired focus positions may lie in a second transverse plane that delimits the available scan field longitudinally in the other direction. If required, further desired focus positions may lie in one or more transverse intermediate planes that lie between the two terminal transverse planes of the first and second groups of desired focus positions. Alternatively or additionally, the desired focus positions may include a group of focus positions that are arranged in a distributed manner along a helical line, the helix axis of which runs parallel to the direction of propagation of the radiation.

In order to obtain a measure of the positioning precision of the scan components, the control arrangement can be set up to ascertain deviations between the desired focus positions and the actual focus positions and to compare the ascertained deviations with at least one predetermined deviation threshold. Particularly when the number of desired focus positions to be tested which are predetermined by the test scan pattern is comparatively small, for example within the low two-digit range, there may be a requirement that no positioning errors must arise, that is to say, all the desired/actual deviations must lie within the limits given by the at least one deviation threshold. In other cases, on the other hand, a certain number of positioning errors may be tolerable. In any case, in the embodiments of the invention a predetermined maximum number of positioning errors (deviations exceeding an associated deviation threshold) can be set for those cases in which the ascertained deviations exceed an associated deviation threshold. This maximum number may be either zero or a value different from zero. The control arrangement can be set up to enable operation of the laser device with the laser source turned on only when only at most so many ascertained deviations exceed an associated deviation threshold as is predetermined by the maximum number. Otherwise the control arrangement can disable the laser device with respect to operation with the laser source switched on, so that no laser machining is possible. In the case of unsuccessful implementation of the test-mode operation, the control arrangement can be set to enter a disabling mode which, for example, can be configured in such a way that the control arrangement can exit it only after successful implementation of a further test-mode operation of the scan components.

BRIEF DESCRIPTION OF THE DRAWINGS

The invention will be elucidated in more detail below on the basis of the appended drawings.

DETAILED DESCRIPTION

Figure 1:
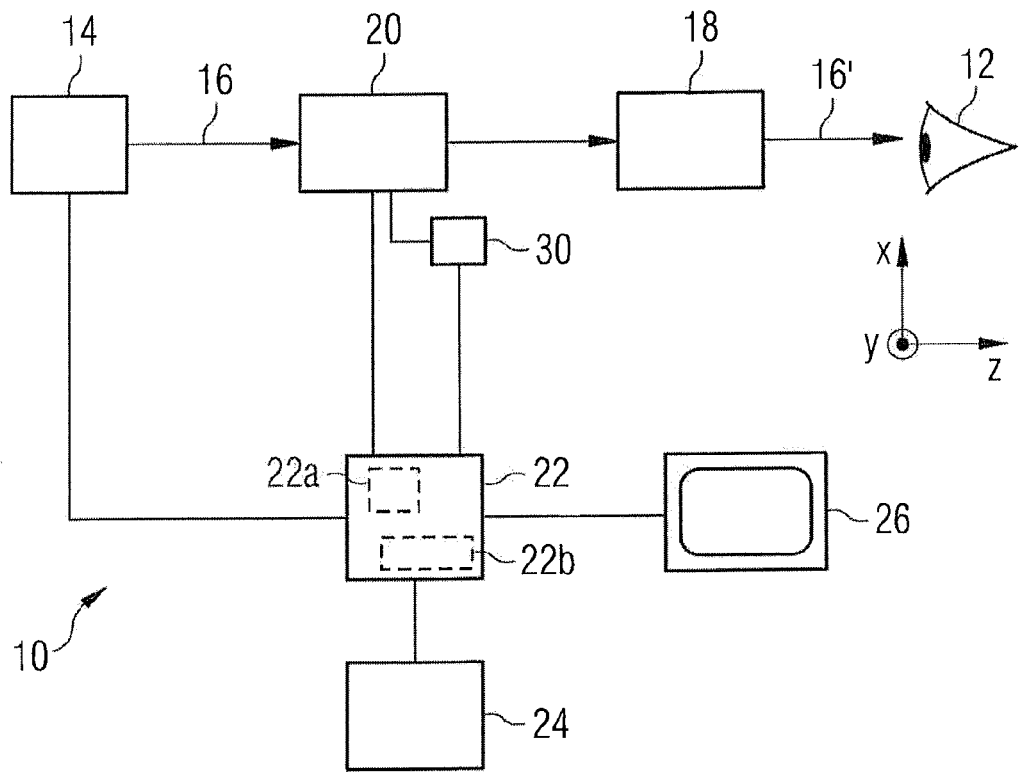
FIG. 1: in schematic block representation, elements of a laser device according to an exemplary embodiment of the present invention.

The laser device shown in FIG. 1—denoted therein generally by 10—serves for machining an object, shown in the exemplary case as a human eye 12, by means of ultra-short-pulse focused laser radiation. 'Ultra-short-pulse' here means pulse durations within the range from femtoseconds to at most single-digit picoseconds, which is exemplary as the embodiments of the present invention can be configured for use with any laser system having a laser scanning functionality. The effect utilized for the machining is the so-called laser-induced optical breakthrough, which results in a photodisruption within the material being machined (here, eye tissue). By placing a plurality of such photodisruptions side by side, diverse incision figures can be generated in the eye 12 and, therein above all, in the cornea.

The laser device 10 includes a laser source 14, which can be a femtosecond laser source, which provides a laser beam 16 which after passing through an optical path-length, along which various elements for beam guidance and shaping are arranged, impinges on the eye 12 as a focused laser beam 16'. The aforementioned elements for beam guidance and shaping include focusing optics 18—constituted, for example, by an f-theta objective—as well as scan components 20 indicated here schematically by a single block.

It is to be emphasized that the representation of the focusing optics 18 and of the scan components 20 in FIG. 1 as separate blocks serves solely for the purpose of better illustration. It is readily conceivable that some of the optical components responsible for the focusing of the laser beam 16 may also assume scan functionality. For instance, it is not ruled out that one or more lenses contained in the focusing optics 18 or even the focusing optics 18 as a whole is/are adjustable for the purpose of longitudinal positioning of the beam focus in the direction of beam propagation. Nevertheless, in a desirable configuration the optical components serving for the scanning of the laser beam 16 are separated from the optical components serving for focusing the laser beam 16 and are consequently arranged outside the focusing optics 18.

For example, the scan components for transverse scanning of the laser beam 16 may include a pair of rotatably arranged deflecting mirrors, the axes of rotation of which are perpendicular to one another, and also, assigned to each of the deflecting mirrors, an individually controllable galvanometer drive. Such galvanometrically actuated deflecting mirrors are known to those having skill in the art; there is therefore no need for any more detailed elucidation of them at this point.

For the purpose of longitudinal scanning of the beam focus, the scan components 20 may, for example, utilize a lens which is provided as part of beam-expanding optics (not represented in any detail) and which for the purpose of varying the divergence of the laser beam 16 is adjustably arranged in the direction of beam propagation or is adjustable as regards its refractive power. An associated actuator in the form of a linear drive or in the form of a controllable voltage-source may then likewise be part of the scan components 20.

In a minimal format of the laser device 10 the scan components 20 are in any case designed for transverse scanning of the laser beam 16. In a more desirable configuration the scan components 20 can also be set up for longitudinal scanning. Incidentally, it will be understood that, in addition to the aforementioned exemplary configurations of the scan components, other principles of action may find application that enable a transverse or/and longitudinal scanning, for example a controlled beam deflection in an electro-optical crystal or an influencing of the divergence of the laser beam by deformation of an optical mirror arranged in the path of propagation of the laser beam 16.

The embodiments of the laser device 10 of the present invention can include, in addition, a processor-based control arrangement 22 for controlling the operation of the laser device. The control arrangement 22 is program-controlled; the control program of the control arrangement 22 is saved in a memory arrangement 24.

Even though the control arrangement 22 in FIG. 1 is represented by a single block, it will be understood that its control functions can be split up to various control modules which can be incorporated into different modules on separate controller boards. For instance, the control arrangement 22 may include a scan control module, drawn with dashed lines at 22a, which is responsible for the control of the scan components 20 and together with these—or together with at least some of the scan components 20—is integrated into a scanner which has been preassembled as a separate component. The remaining control functions of the control arrangement 22 can, for example, be combined in a central control module 22b (likewise indicated by dashed lines) situated structurally outside this scanner, which is responsible, inter alia, for the synchronization of the operation of the laser source 14 and the operation of the scan components 20 and is able to send corresponding control commands to the scan control module 22a in order to start a scan procedure. The concrete adjusting operations for setting the scan components 20 can then be controlled by the scan control module 22a in accordance with suitable scan data which were previously loaded into the scan control module 22a and which define a scan pattern to be executed.

Corresponding to the possible splitting of the control arrangement 22 into separate control modules, the memory arrangement 24 can also be split up into separate memory modules, and the aforementioned control program can be split up into separate program modules which, in turn, can be stored in various memory modules. For example, a memory module can be integrated, jointly with the scan control module 22a, into the aforementioned scanner and can store such program parts that are necessary for the control of the scan components 20. One or more further memory modules, on the other hand, can be assigned to the central control module 22b and may store the remaining program parts of the control program.

Connected furthermore to the control arrangement 22 is an output unit 26, here shown in exemplary form as a monitor, on which test results yet to be elucidated can be output which are obtained within the scope of a test-mode operation of the laser device 10. Even though not represented in any detail in FIG. 1, alternatively or additionally to the monitor 26 a printer can be linked to the control arrangement 22, in order to output the aforementioned test results in printed form. In FIG. 1 a triaxial coordinate frame has in addition been drawn in which, according to conventional notation, spans an x-y transverse plane orthogonal to the direction of propagation of the radiation of the laser beam 16, whereas the z-axis defines the longitudinal direction of beam propagation.

The control arrangement 22 of the embodiments of the present invention can be set up to implement, with the laser source 14 turned off, a test-mode operation in which the scan components 20 or at least some of the same are controlled in accordance with a predetermined test scan pattern. This dry run, in which no laser radiation is given off from the laser source 14, is intended to enable a positional check by which it is to be ensured that the entire region in which the beam focus in the x-, y- and, where appropriate, z-directions can be nominally set can be traversed with precision. In particular, the positional check is to enable an examination of any possible desired/actual deviations of the focus position in the entire scan region. The maximal scan region, which in the present case—on the assumption of both transverse and longitudinal scan capability—is a three-dimensional space, is also designated here as the available scan field.

Measuring components 30 indicated schematically as a single block can be provided for the purpose of registering the actual setting condition of at least some of the scan components 20 metrologically and supplying corresponding measured values to the control arrangement 22. The latter is able to calculate values for the actual position of the beam focus from the measured values supplied. For example, for the purpose of registering the actual position of a rotatable deflecting mirror contained in the scan components 20 the measuring components 30 may include a position-detector as shown and described in European Patent EP 1 295 090 B1, which is hereby incorporated by reference in its entirety.

The calculated actual focus positions can be stored by the control arrangement 22 in the memory arrangement 24, assigned to associated desired focus positions. In the course of a machining of an eye 12, the desired focus positions are predetermined, for example in tabular form, by specification of the respective x-, y- and z-values. After conclusion of the machining of the eye 12, the control arrangement 22 can compare the actual values of the focus position, ascertained in the meantime, with the associated desired values and can output corresponding information via the monitor 26 or an attached printer. A user, such as an operating surgeon, or an evaluating program operating automatically can establish, on the basis of the results of the desired/actual comparisons, whether the scan system is operating with the demanded high precision in the entire available scan space.

The aforementioned test-mode operation of the embodiments of the present invention is expedient, above all, when (but not only when) during the scan operation of the laser device 10 measured values for actual focus positions can indeed be recorded and stored by means of the measuring components but the laser device 10 has not been set up to evaluate the actual focus positions during the scan operation with regard to deviations from the associated desired focus positions and, where appropriate, to intervene in a corrective manner if impermissibly large deviations arise. Such circumstances may obtain, for example, if the desired and actual data of the focus positions cannot be transmitted from the scan control module 22a to the central control module 22b during a scan procedure, but rather the central control module 22b obtains access to these data only after conclusion of the scan procedure. In this way, the test-mode operation enables an advance inspection of the positioning quality of the scan components 20. Depending on the result of the test-mode operation, it may turn out that the precision of the scan in the available scan field is sufficiently high in order to implement a planned machining of an eye, or measures such as an exchange of at least some of the scan components may be necessary, should the accuracy of the scan prove to be insufficient.

The test-mode operation can be implemented by the control arrangement 22, for example, in response to a start command, input by the user, for implementing a laser machining (for instance, for the purpose of generating a flap incision within the scope of a LASIK operation on the eye 12), in which connection the control arrangement begins the laser machining only when the test-mode operation has previously been implemented successfully. Otherwise it can, for example, output a suitable warning message on the monitor 26, to draw the attention of the operating surgeon to the fact that the test-mode operation was unsuccessful and for this reason the planned laser machining cannot be carried out.

Figure 2:
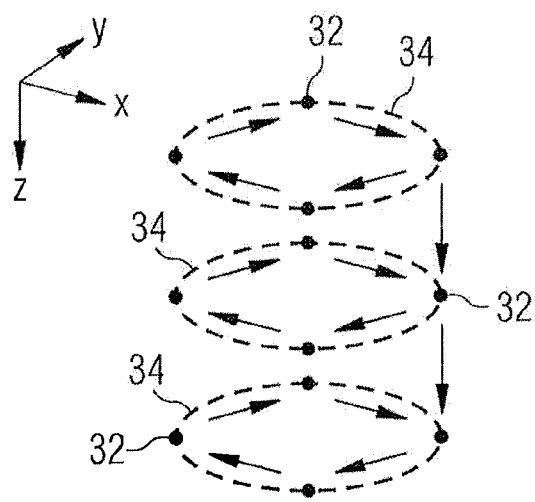
FIG. 2: an example of a test scan pattern for the laser device shown in FIG. 1, consisting of discrete desired focus positions.

For an explanation of a test scan pattern processed within the scope of the test-mode operation, reference will now additionally be made to FIG. 2. The exemplary test scan pattern of FIG. 2 is composed of a plurality of discrete desired focus positions 32, the x-, y- and z-coordinate values of which were previously loaded into the control arrangement 22, and therein in particular into the scan control module 22a. Within the scope of the test-mode operation the scan components 20 are set in such a way that the predetermined desired focus positions are traversed in rapid succession. In the process the scan components 20 are controlled continuously until such time as a desired focus position has been reached. The control of the scan components 20 are then stopped for a short time before the scan components 20 are adjusted anew in order to traverse the next desired focus position. To this extent the procedure for adjusting the scan components 20 is a stepwise process, as distinct from a continuous sweeping of a predetermined path.

In the exemplary case of FIG. 2 which is shown, the desired focus positions 32 have been split up into several (here, three) groups which are respectively assigned to an x,y transverse plane. In each transverse plane the desired focus positions 32 of the group in question are arranged in a distributed manner along an imaginary circular line 34 at regular angular distances. The imaginary circular lines 34 are indicated by dashed lines in FIG. 2. Overall, in the exemplary case shown in FIG. 2 four desired focus positions 32 are predetermined per circular line 34, that is to say, one desired focus position per quadrant. It will be understood that the number of desired focus positions 32 per transverse plane may differ from this, in particular it may also be greater. Similarly it will be understood that, departing from the exemplary case shown, where the number of desired focus positions 32 in each transverse plane is the same, this number may be different for various transverse planes.

In the exemplary case shown in FIG. 2 the desired focus positions 32 are situated longitudinally above one another in the various transverse planes, that is to say, they are in register with one another in the z-direction. This too is not a necessity; for example, it is contemplated as being within the scope of the invention to choose an arrangement figure of the desired focus positions 32 in which they are angularly offset with respect to one another from transverse plane to transverse plane.

The temporal sequence in which the desired focus positions 32 are traversed can be chosen arbitrarily. In a desirable embodiment of the invention all the desired focus positions in a transverse plane are first traversed before changing to the next transverse plane. Within a transverse plane the desired focus positions can be traversed, for example, individually in succession along the circular line 34 in question.

On the assumption of a circular cylindrical available scan field (i.e. a scan field, the transverse outer boundary of which is circular), the circular lines 34 can run, for example, along the outer boundary of this available scan field, so that the desired focus positions 32 serve, above all, to test the precision of the scan at the outer boundaries of the available scan field. It is nevertheless contemplated as being within the scope of the invention to arrange the desired focus positions 32 within the available scan field at a distance from the outer boundaries thereof if a positional check of the inner regions of the available scan field is desirable.

After one of the desired focus positions 32 has been traversed and a brief control stop of the scan components 20 takes place, the actual focus position is registered and stored, assigned to the desired focus position 32 in question, by means of the measuring components 30. The measurement accordingly takes place at a standstill of the scan system, that is to say, during a stop of the scan movement. In order to eliminate settling-processes in the measured result, after a desired focus position has been reached a wait is observed for a certain time before the measurement is carried out, for example, for a few milliseconds.

The scan movement can then be continued and the next desired focus position is traversed. This is repeated in succession for all the desired focus positions 32. It may be sufficient to take into account and to store for the desired focus positions 32 or/and the actual focus positions only one or two coordinates instead of all three coordinates of the xyz coordinate system. For the desired focus positions 32 of the test scan pattern according to FIG. 2 it may, for example, suffice to represent the desired focus positions and/or the actual focus positions only by the z-coordinate value and a transverse coordinate value, for instance the x-coordinate value. To the extent that the laser device 10 enables this, however, it may be desirable to register all three coordinate values for all the desired focus positions 32 and assigned actual focus positions.

After execution of the test scan pattern, the control arrangement 22 undertakes an analysis of the registered actual focus positions with regard to deviations from the desired focus positions. In this connection it compares the deviations found with at least one predetermined threshold. For example, the control arrangement 22 may ascertain the deviations between the desired focus positions and the actual focus positions separately for each coordinate axis individually and compare them with an assigned deviation threshold. The deviation threshold to be applied may be the same for the coordinate axes or different for different coordinate axes. If desired, the control arrangement 22 may additionally ascertain an overall deviation from the deviations found along the individual coordinate axes, for instance in the manner of the Euclidean distance. It can also compare the overall deviation found in this way with an assigned deviation threshold. It will be understood that each deviation threshold may either be permanently predetermined or capable of being selected by the user via an input unit, not represented in any detail in the Figs., connected to the control arrangement 22.

In the best case, all the actual focus positions lie within the given deviation limits. If an actual focus position differs from an assigned desired focus position 32 by an impermissibly large extent, the control arrangement 22 can instigate the output of a warning on the monitor 26. The warning informs the user that the precision of the scan is not sufficient. As a further response, the control arrangement 22 can enter a disabling mode which prohibits operation of the laser device 10 with the laser source 14 turned on. After successful implementation of a further test-mode operation, in which all the registered actual focus positions have remained within the given deviation limits, the control arrangement 22 can exit the disabling mode and enable the operation of the laser device 10 with the laser source 14 turned on.

Alternatively or additionally, the control arrangement 22 can be set up to output the registered actual focus positions together with the desired focus positions and/or the ascertained desired/actual deviations without further analysis on the monitor 26 or in some other form. In this case the assessment of the test result can be left to the user.

The test-mode operation of the embodiments of the present invention described above serves for inspecting the static behavior of the scan system, in particular the precision of the position-finding, and additionally for inspecting whether all signal paths are operating correctly, for instance an analogue signal line from a driver pcb to a scanner servo and also a return channel from an encoder (part of the measuring components 30) to the control arrangement 22.

Although embodiments of the proposed system and technique of the present invention have been illustrated in the accompanying drawings and described in the description, it will be understood that the invention is not limited to the embodiments disclosed herein. In particular, the proposed technique is capable of numerous rearrangements, modifications and substitutions without departing from the scope of the invention as set forth and defined by the following claims.

The invention claimed is:

1. A laser device, in particular for ophthalmological laser surgery, including:
   a laser source for providing laser radiation;
   controllable scan components for setting a focus position of the laser radiation;
   measuring components for registering information that is representative of an actual position of the radiation focus;
   a control arrangement controlling the laser source and the scan components, wherein the control arrangement has been set up to bring about the implementation of a test-mode operation of at least some of the scan components with the laser source turned off, in accordance with a predetermined test scan pattern, the test scan pattern representing a plurality of discrete desired focus positions to be traversed in succession, and the control arrangement having been set up to stop, at each of the desired focus positions, the scan movement of the scan components and to ascertain, assigned to each of the desired focus positions, respectively, an actual focus position on the basis of the registered information of the measuring components.

2. The laser device according to claim 1, wherein the desired focus positions include at least one group of focus positions which are arranged in distributed manner in a transverse plane orthogonal to the direction of propagation of the radiation.

3. The laser device according to claim 2, wherein the desired focus positions include at least one group of focus positions which are arranged in distributed manner in the transverse plane along a circular line, preferentially at regular angular distances.

4. The laser device according to claim 1, wherein at least some of the desired focus positions are arranged in distributed manner in the direction of propagation of the radiation.

5. The laser device according to claim 4, wherein the desired focus positions include several groups of focus positions which are arranged in distributed manner in various transverse planes orthogonal to the direction of propagation of the radiation.

6. The laser device according to claim 1, wherein at least a fractional number of the desired focus positions are arranged at the margin of a given maximal scan field.

7. The laser device according to claim 1, wherein all the desired focus positions are arranged at the margin of a given maximal scan field.

8. The laser device according to claim 1, wherein the control arrangement has been set up to ascertain deviations between the desired focus positions and the actual focus positions and to compare the ascertained deviations with at least one predetermined deviation threshold.

9. The laser device according to claim 8, wherein the control arrangement has been set up to enable operation of the laser device with the laser source turned on only when no more than a predetermined maximum number of ascertained deviations exceed an associated deviation threshold, preferentially when none of the ascertained deviations exceeds the associated deviation threshold.

* * * * *